(12) United States Patent
Chen

(10) Patent No.: US 10,494,403 B2
(45) Date of Patent: Dec. 3, 2019

(54) CYCLOPEPTIDE, PHARMACEUTICAL OR COSMETIC COMPOSITION COMPRISING THE SAME AND METHOD FOR PREPARING THE SAME

(71) Applicant: Ciphore Biomed Technology Limited Company, Taipei (TW)

(72) Inventor: Po-Ruay Chen, Taipei (TW)

(73) Assignee: CIPHORE BIOMED TECHNOLOGY LIMITED COMPANY, Taipei (TW)

( * ) Notice: Subject to any disclaimer, the term of this patent is extended or adjusted under 35 U.S.C. 154(b) by 0 days.

(21) Appl. No.: 15/912,639

(22) Filed: Mar. 6, 2018

(65) Prior Publication Data

US 2019/0276497 A1 Sep. 12, 2019

(51) Int. Cl.
| C07K 7/64 | (2006.01) |
| A61K 8/64 | (2006.01) |
| A61K 38/12 | (2006.01) |

(52) U.S. Cl.
CPC .......... *C07K 7/64* (2013.01); *A61K 8/64* (2013.01); *A61K 38/12* (2013.01)

(58) Field of Classification Search
None
See application file for complete search history.

(56) References Cited

U.S. PATENT DOCUMENTS

2002/0032306 A1* 3/2002 Jonczyk ............... C07K 14/75
530/317

FOREIGN PATENT DOCUMENTS

| DE | 4310643 A1 | 10/1994 |
| DE | 19613933 A1 | 10/1997 |
| WO | 2009124754 A1 | 10/2009 |

OTHER PUBLICATIONS

Olaf Prante,Urgen Einsiedel,Roland Haubner,Peter Gmeiner,Hans-Jurgen Wester,Torsten Kuwert, and Simone Maschauer, 3,4,6-Tri-O-acetyl-2-deoxy-2-[18F]fluoroglucopyranosyl Phenylthiosulfonate: A Thiol-Reactive Agent for the Chemoselective 18F-Glycosylation of Peptides, Bioconjugate Chem. 2007, 18, 254-262.
Roland Haubner,Rainer Gratias,Beate Diefenbach,Simon L. Goodman,Alfred Jonczyk, and Horst Kessler, Structural and Functional Aspects of RGD-Containing Cyclic Pentapeptides as Highly Potent and Selective Integrin RVâ3 Antagonists, J. Am. Chem. Soc. 1996, 118, 7461-7472.
Haubner, R.; Gratias, R.; Goodman, S. L.; Kessler, H., RGD plus X: Structure/activity investigations on cyclic RGD-peptides, Chemistry, Structure and Biology, Proceedings of the American Peptide Symposium, 14th, Columbus, Ohio, Jun. 18-23, 1995 (1996), 205-206.

* cited by examiner

*Primary Examiner* — Maury A Audet
(74) *Attorney, Agent, or Firm* — Bacon & Thomas, PLLC

(57) ABSTRACT

A cyclopeptide is disclosed, which is represented by the following formula (I) or (I'):

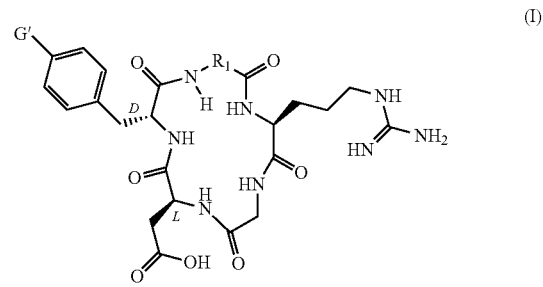

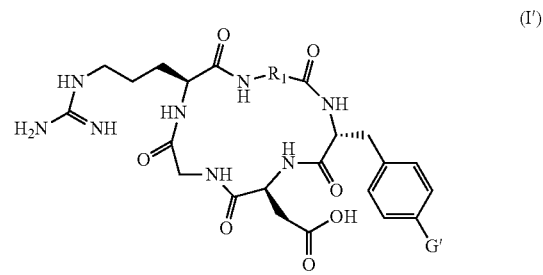

wherein $R_1$ and G' are defined in the specification. In addition, a pharmaceutical or cosmetic composition comprising the same and a method for preparing the same are also disclosed.

20 Claims, No Drawings

CYCLOPEPTIDE, PHARMACEUTICAL OR COSMETIC COMPOSITION COMPRISING THE SAME AND METHOD FOR PREPARING THE SAME

BACKGROUND OF THE INVENTION

1. Field of the Invention

The present invention relates to a cyclopeptide, a pharmaceutical or cosmetic composition comprising the same and a method for preparing the same. More specifically, the present invention relates to a topical or cosmetic skin care cyclopeptide, a pharmaceutical or cosmetic composition comprising the same and a method for preparing the same.

2. Description of Related Art

Peptides have found widespread use in various fields, for example, topical or cosmetic skin care uses. Among the known peptides, the peptide with arginine (R)-glycine (G)-aspartate (D) motif is found as a common element in cellular recognition.

It is known that the peptide containing RGD motif can bind to the intergrin ROD binding site, and can be used to coat synthetic scaffolds in tissue engineering to enhance cellular attachment by mimicking in vivo conditions.

In the conventional method for preparing the peptide containing RGD motif, coupling agents have to be used to catalyze the peptide synthesis. However, the used amount of the coupling agents is not less, and the cost of the coupling agents itself is high. Hence, the production cost of the peptide is not low, and the obtained peptide cannot be available to all.

Therefore, it is desirable to provide a novel peptide containing RGD motif and a novel method for preparing the peptide; so, the obtained peptide can be widely applied to various fields.

SUMMARY OF THE INVENTION

The object of the present invention is to provide a novel cyclopeptide and a pharmaceutical or cosmetic composition comprising the same.

The RGD- and GRD-cyclopeptides of the present invention are respectively represented by the following formula (I) and (I'):

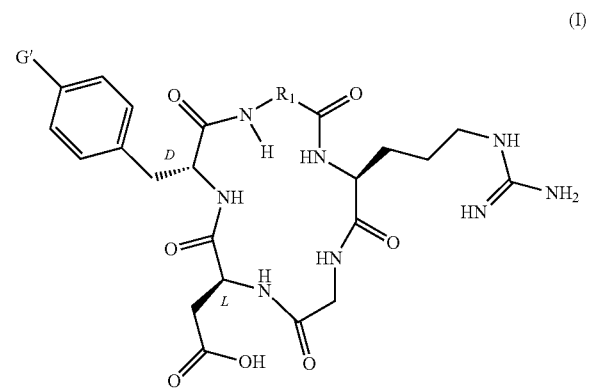
(I)

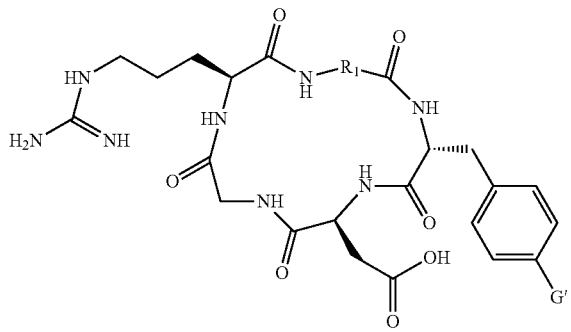
(I')

wherein, $R_1$ is

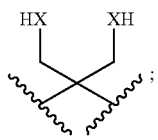

X is O, S, or N—$R_2$, in which $R_2$ is H, $C_{1-6}$ alkyl, $(CH_2CH_2O)_nH$—$C(=O)$—$C_{1-10}$ alkyl, or $C(=O)(C_2H_4)_2C(=O)O(C_2H_4O)_nH$, in which n=1-3; and G' is H or OH.

The pharmaceutical or cosmetic composition of the present invention comprises: an excipient or a metal (II) sulfate; and the aforementioned cyclopeptide of the present invention.

In the cyclopeptide and the pharmaceutical or cosmetic composition of the present invention, X preferably is O, S, or N—$R_2$, in which $R_2$ is H, $C_{1-6}$ alkyl, —$C(=O)$—$C_{4-10}$ alkyl, $(CH_2CH_2O)_nH$, or $C(=O)(C_2H_4)_2C(=O)O(C_2H_4O)_nH$, in which n=1-3. In one exemplary embodiment of the present invention, X is O.

In one preferred aspect of the present invention, the cyclopeptide of the present invention can be represented by the following formula (I-1) or (I'-1):

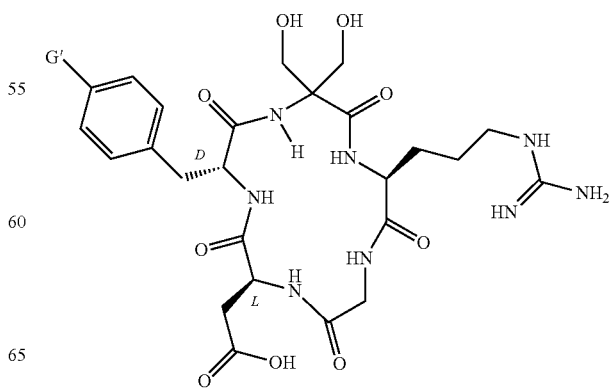
(I-1)

-continued

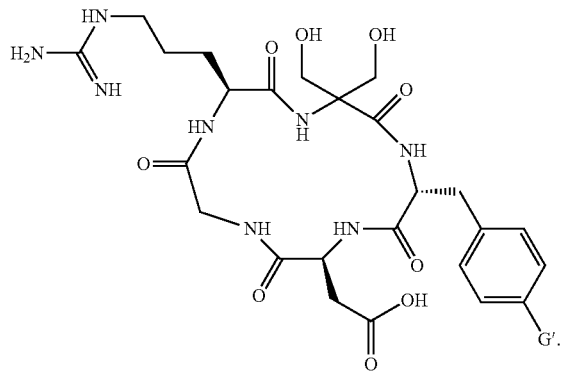
(I'-1)

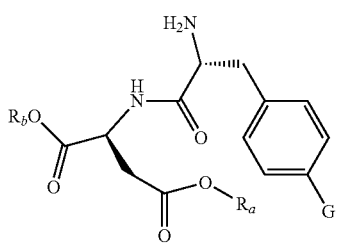
(II'-1)

$R_c$—NH—$R_1$—COOH (II-2)

Herein, each of $R_a$ and $R_b$ independently is alkyl, cycloalkyl, aryl or heteroaryl;

each of $R_c$ and $R_d$ is a protection group;

$R_1$ is

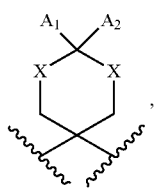

in which each of $A_1$ and $A_2$ independently is H, $C_{1-6}$ alkyl or esters, or $A_1$, $A_2$ and carbon attached to $A_1$ and $A_2$ together form $C_{5-8}$ cycloalkyl; X is O, S, or N—$R_2$, in which $R_2$ is H, $C_{1-6}$ alkyl, $(CH_2CH_2O)_nH$, $C(=O)$—$C_{1-10}$ alkyl, or $C(=O)(C_2H_4)_2C(=O)O(C_2H_4O)_nH$, in which n=1-3; and G is H or O-t-Bu.

The cyclopeptide of the present invention comprises amino acids of arginine (R), glycine (G) and aspartate (D), which can bind to the intergrin RGD binding site. When the cyclopeptide of the present invention binds to the intergrin RGD binding site of the skin, the communication process between dermis and epidermis can be revived, and the production of important proteins of the basement membrane can be stimulated. Therefore, the purpose of ameliorating scars, wounds, inflammatory processes, aging and/or wrinkle formation can be achieved. Hence, the cyclopeptide and the pharmaceutical or cosmetic composition of the present invention can be applied to topical or cosmetic skin care composition.

In one aspect of the pharmaceutical or cosmetic composition of the present invention, the suitable excipient for the present invention can be any excipient used in the art, for example, a binder, an anti-adhesive agent, a dispersant and a lubricant.

In another aspect of the pharmaceutical or cosmetic composition of the present invention, the metal (II) sulfate can be $Cu^{2+}$ sulfate or $V(O)^{2+}$ sulfate.

In further another aspect of the pharmaceutical or cosmetic composition of the present invention, the excipient and the metal (II) sulfate can be used in combination.

Except for the aforementioned cyclopeptide and pharmaceutical or cosmetic composition of the present invention, another object of the present invention is to provide a novel bio-compatible, catalytic method for preparing the cyclopeptide of the present invention.

The method of the present invention comprises the following steps (A) to (D).

In the step (A), compounds represented by the following formulas (II-1) or (II'-1), and (II-2) are provided from commercial source or made by our catalytic methods.

In the step (B), a reaction between the compounds of formulas (II-1) or (II'-1) and (II-2) is performed to obtain a compound represented by the following formula (II-3) and (II'-3), respectively,

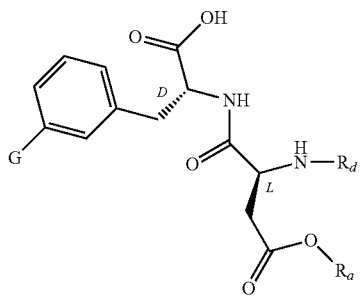
(II-1)

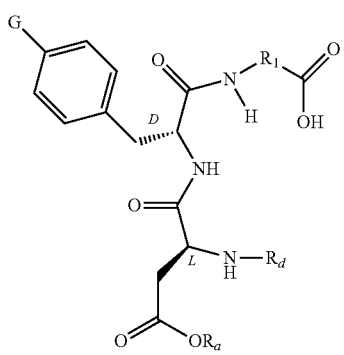
(II-3)

and

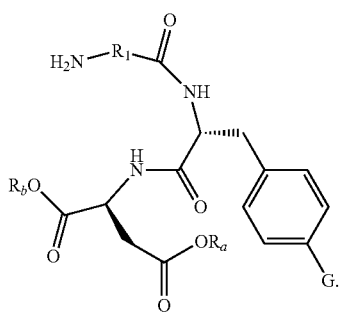

(II'-3)

In the step (C), a reaction between the compound of formula (II-3) or (II'-3) and a compound represented by the following formula (II-4) or (II'-4), respectively, is performed to obtain a compound represented by the following formula (II-5) and (II'-5), respectively.

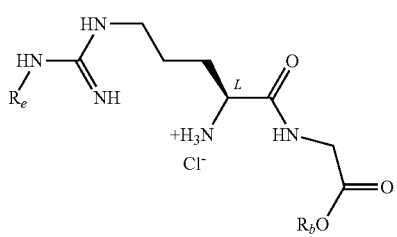

(II-4)

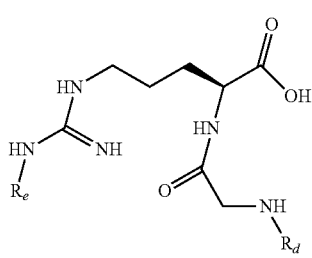

(II'-4)

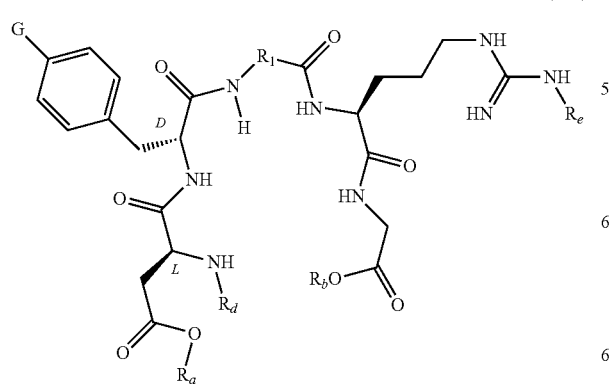

(II-5)

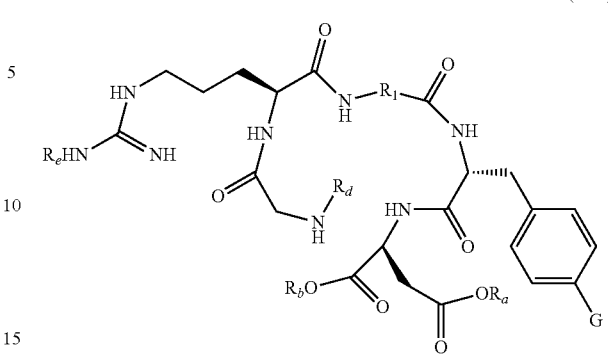

(II'-5)

Herein, each of $R_d$ and $R_e$ independently is a protection group.

In the step (D), a cyclization reaction of the compound of formula (II-5) or (II'-5) is performed with a catalyst of formula (III), to obtain a compound represented by the formula (I) or (I'), respectively.

$$M(O)_m L^1_y L^2_z \qquad (III)$$

Herein, M is a metal selected from the group consisting of IVB, VB, VIB and actinide groups;
$L^1$ and $L^2$ respectively is a ligand;
m and y are integers of greater than or equal to 1; and
z is an integer of greater than or equal to zero.

In the method of the present invention, $R_c$ and $R_d$ can be Fluorenylmethyloxycarbonyl (Fmoc); and $R_e$ can be MTr (4-methoxy-2,3,6-trimethylbenzenesulphonyl). However, the present invention is not limited thereto.

In the method of the present invention, the reaction between the compounds of formulas (II-1) or (II'4) and (II-2) or the reaction between the compound of formula (II-3) and (II-4) or (II'-3) and (II'-4) can be performed with the catalyst of formula (III) or a coupling agent.

In the method of the present invention, when the reactions in the steps (B) to (D) are performed with the catalyst of formula (III), the catalyst used in the steps (B) to (D) can be the same or different.

In the catalyst of formula (III), $L^1$ is a ligand, which preferably is selected from the group consisting of Cl, OTf, OTs, NTf$_2$, halogen, RC(O)CHC(O)R, OAc, OC(O)CF$_3$, OEt, O-iPr, and butyl, in which R is alkyl (preferably, $C_{1-6}$ alkyl; more preferably, $C_{1-3}$ alkyl). In addition, $L^2$ is also a ligand, which preferably is selected from the group consisting of Cl, H$_2$O, CH$_3$OH, EtOH, CH$_3$CN and

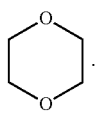

Furthermore, in the catalyst of formula (III), M can be a metal selected from the group consisting of IVB, VB, VIB and actinide groups. In one aspect, M is a group IVB transition element, m is 1 and y is 2; wherein. M can be Ti, Zr of W. In another aspect, M is a group VB transition element, in is 1 and y is 2 or 3; wherein M can be V or Nb. In another aspect, M is a group VIB transition element, m is 1 and y is 4; wherein M is Mo, W or Cr. In another aspect, M is a group VIB transition element, m is 2 and y is 2; wherein M is Mo, W or Cr. In further another aspect, M is selected from the actinide group, m is 2 and y is 2; wherein M is U. Specific examples for the catalyst of formula (III) can be $MoO_2Cl_2$, $V(O)OCl_2$, $V(O)(OAc)_2$, $V(O)(O_2CCF_3)_2$, $Ti(O)(acac)_2$, $Zr(O)Cl_2$, $Hf(O)Cl_2$, $Nb(O)Cl_2$, $MoO_2(acac)_2$, $V(O)(OTs)_2$, $V(O)(NTf_2)_2$, or $VO(OTf)_2$, but the present invention is not limited thereto.

Furthermore, in the catalyst of formula (III), z can be an integer of greater than or equal to zero; and preferably, z is 0.

In the conventional method for preparing the cyclopeptide, 3-5 equivalent of coupling agents such as Hydroxybenzotriazole (HOBO, 1-Hydroxy-7-azabenzotriazole (HOAt), 2-(1H-benzotriazol-1-yl)-1,1,3,3 tetramethyluronium hexafluorophosphate (HBTU) and benzotriazol-1-yloxytripyrrolidinophosphonium hexafluorophosphate (PyBOP) are used. Because these coupling agents are expensive, the obtained cyclopeptide cannot be easily commercialized and applied to various fields.

In the method for preparing the cyclopeptide of the present invention, the catalyst of formula (III) is water soluble and used to facilitate the reaction progress. Hence, the expensive coupling agents are not used in the method of the present invention. Therefore, cyclopeptide can be produced in a cheaper manner, and the obtained cyclopeptide can be applied to various fields.

In the present invention, alkyl, cycloalkyl, aryl, and heteroaryl present in the compounds include both substituted and unsubstituted moieties, unless specified otherwise. Possible substituents on alkyl, cycloalkyl, aryl, and heteroaryl include, but are not limited to, alkyl, alkenyl, halogen, alkoxy, ketone, alcohol, thioether, carbamate, amino, heterocyclic group or aryl; but alkyl cannot be substituted with alkyl.

In the present invention, the term "halogen" includes F, Cl, Br and I; and preferably is Cl or I. The term "alkyl" refers to linear and branched alkyl; preferably, includes linear and branched $C_{1-20}$ alkyl; more preferably, includes linear and branched $C_{1-12}$ alkyl; and most preferably, includes linear and branched $C_{1-6}$ alkyl. Specific examples of alkyl include, but are not limited to, methyl, ethyl, n-propyl, iso propyl, n-butyl, sec-butyl, iso-butyl, tert-butyl, pentyl, neo-pentyl or hexyl. The term "alkoxy" refers to a moiety that the alkyl defined in the present invention coupled with an oxygen atom; preferably, includes linear and branched $C_{1-20}$ alkoxy; more preferably, includes linear and branched $C_{1-12}$ alkoxy; and most preferably, includes linear and branched $C_{1-6}$ alkoxy. Specific examples of alkoxy include, but are not limited to, methoxy, ethoxy, n-propoxy, iso-propoxy, n-butoxy, iso-butoxy, sec-butoxy, tert-butoxy, pentyloxy, neopentyloxy or hexyloxy. The term "alkenyl" refers to a linear or branched hydrocarbon moiety that contains at least one double bond; preferably, includes a linear and branched hydrocarbon $C_{2-20}$ moiety containing at least one double bond; more preferably, includes a linear and branched hydrocarbon $C_{2-12}$ moiety containing at least one double bond; and most preferably, includes a linear and branched hydrocarbon $C_{2-6}$ moiety containing at least one double bond. Specific examples of alkenyl include, but are not limited to, ethenyl, propenyl, allyl, or 1,4-butadienyl. The term "aryl" refers to a monovalent 6-carbon monocyclic, 10-carbon bicyclic, or 14-carbon tricyclic aromatic ring system. Specific examples of aryl include, but are not limited to, phenyl, naphthyl, pyrenyl, anthracenyl or phenanthryl; and preferably, the aryl is phenyl. The term "heterocyclic group" refers to a 5-8 membered monocyclic, 8-12 membered bicyclic or 11-14 membered tricyclic heteroaryl or heterocycloalkyl having at least one heteroatom which is selected from the group consisting of O, S and N. Specific examples of heterocyclic group include, but are not limited to, pyridyl, pyrimidinyl, furyl, thiazolyl, imidazolyl or thienyl. The term "ester" refers to a moiety derived from a carboxylic acid; preferably, includes linear or branched $C_{1-12}$ ester; and most preferably, includes linear or branched $C_{1-6}$ ester. Specific examples of ester include, but are not limited to, formate, acetate, propanoate, butanoate, pentanoate, or hexanoate.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

The cyclopeptide of one preferred embodiment of the present invention can be prepared as follows.

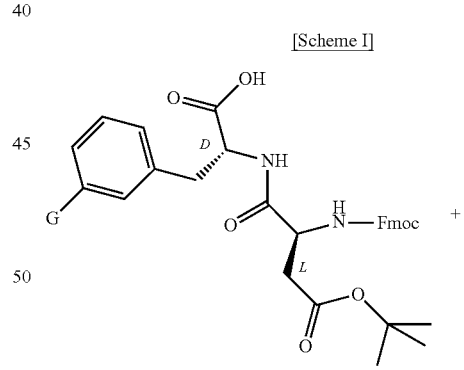

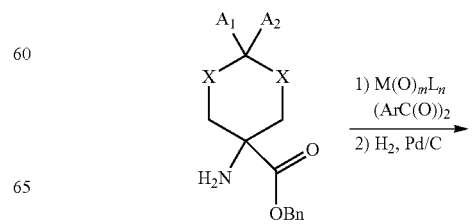

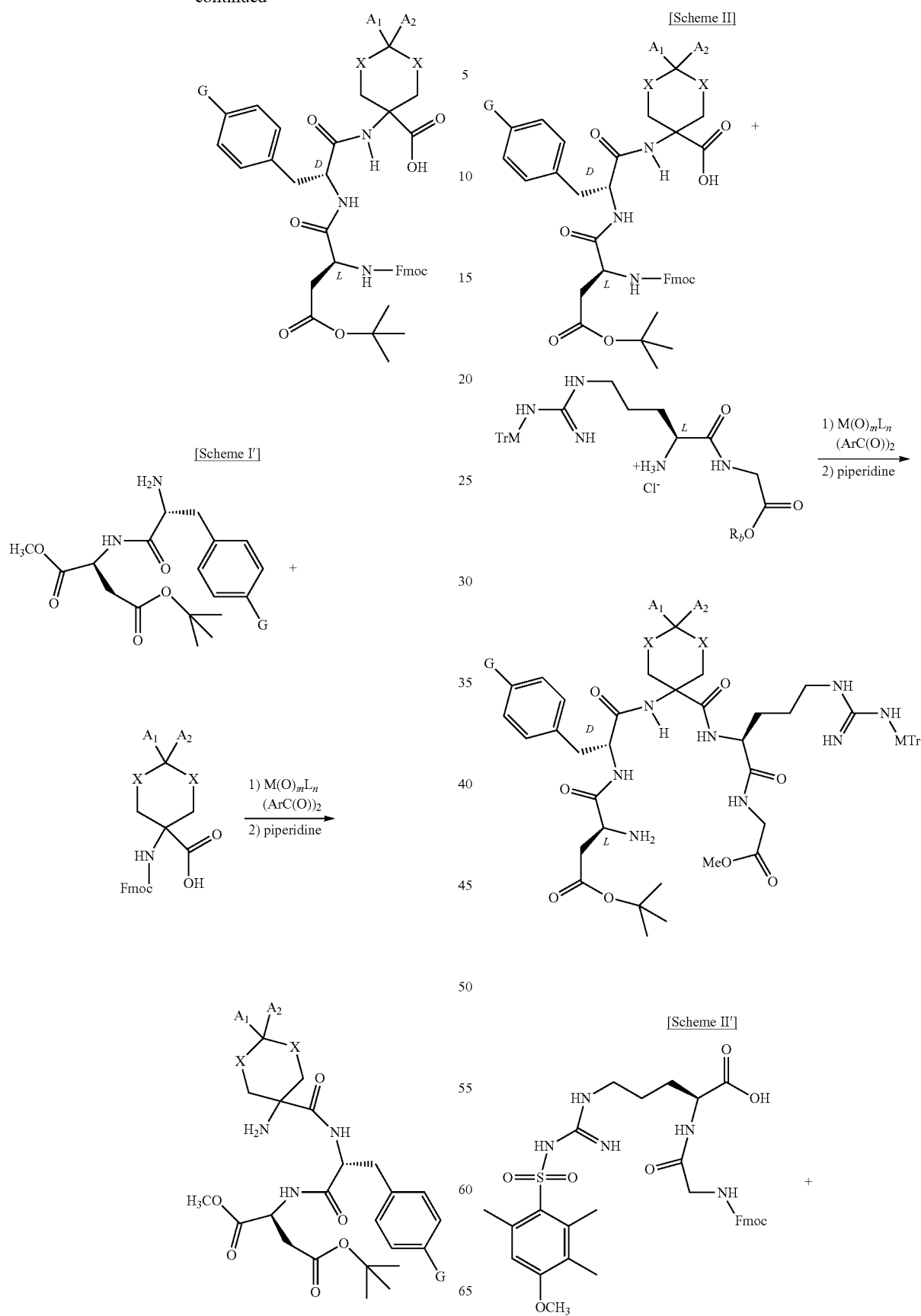

-continued

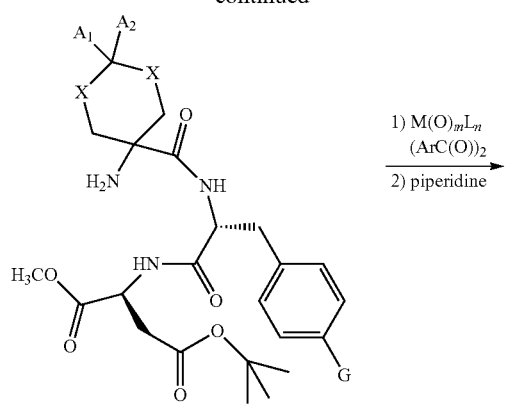

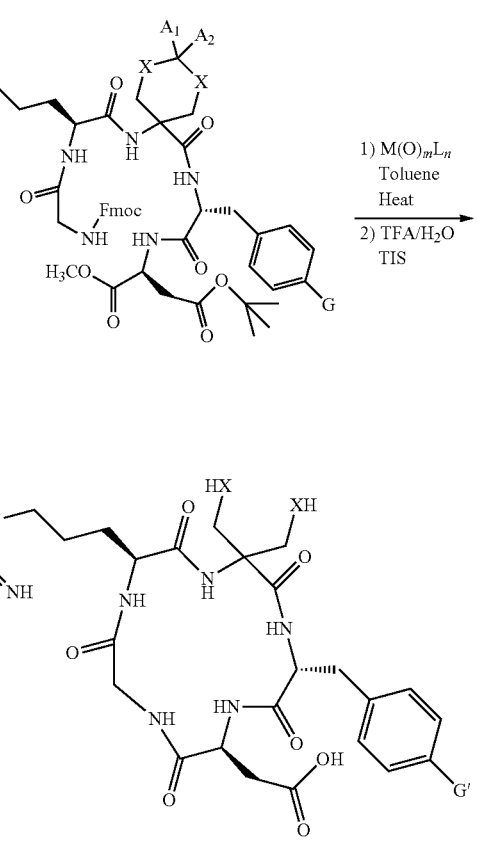

[Scheme III']

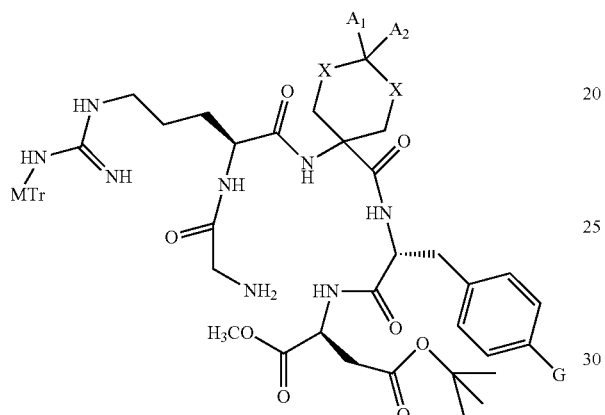

[Scheme III]

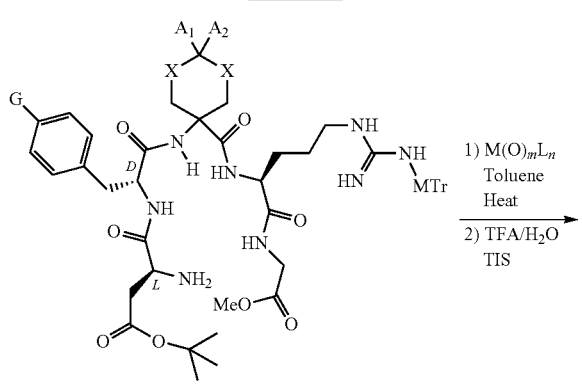

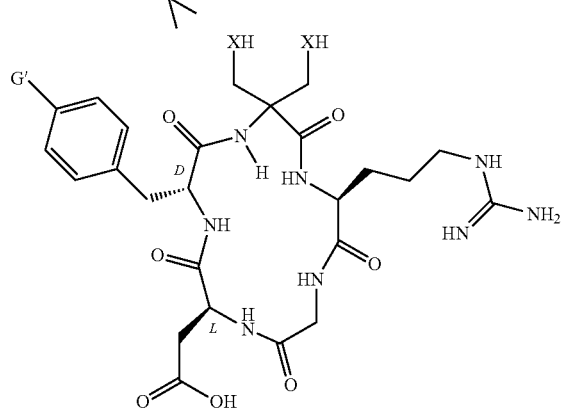

In Scheme I' and II', the coupling agents may also be used and can be, for example, Hydroxybenzotriazole (HOBO, 1-Hydroxy-7-azabenzotriazole (HOAt), 2-(1H-benzotriazol-1-yl)-1,1,3,3-tetramethyluronium hexafluorophosphate (HBTU) and benzotriazol-1-yl-oxytripyrrolidinophosphonium hexafluorophosphate (PyBOP).

Hereinafter, the present invention provides examples for preparing the cyclopeptide of the present invention; but the present is not limited thereto.

Preparation Example 1

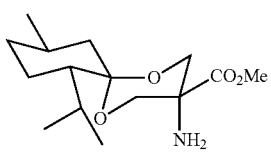

Data: $^1$H NMR (400 MHz, CDCl$_3$): δ=4.42 (d, J=11.8 Hz, 1H), 4.16 (d, J=12.0 Hz, 1H), 3.79 (s, 3H), 3.56-3.60 (m, 2H), 2.72-2.74 (m, 1H), 2.42-2.48 (m, 1H), 1.99 (br. s, 2H), 1.70-1.75 (m, 1H), 1.41-1.54 (m, 3H), 1.24-1.31 (m, 1H), 0.84-0.95 (m, 10H), 0.71 (t, J=12.0 Hz, 1H) ppm. MS (EI): m/z=286 [M+H]$^+$

Preparation Example 2: (Fmoc-amino)-2,2-dimethyl-1,3-dioxane-5-carboxylic Acid (Fmoc-ADM-DOA)

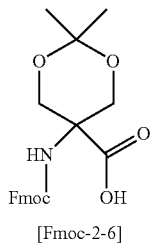

[Fmoc-2-6]

This compound Fmoc-2-6 is prepared following the literature procedure (*J. Pept. Sci.* 2008, 14, 1163). $^1$H NMR (400 MHz, CDCl$_3$) δ 7.77-7.30 (m, 8H, aromatic), 5.81 (bs, 1H, NH), 4.42 (d, J=7.2 Hz, 2H, CH$_2$), 4.27 (t, J=7.2 Hz, 1H, CH), 4.20 (d, J=12.0 Hz, 2H, CH$_2$O), 4.14 (d, J=12.0 Hz, 2H, CH$_2$O), 3.02 (b, 1H, COOH), 1.51 (s, 6H, C(CH$_3$)$_2$).

Preparation Example 3: 5-((Benzyloxy)carbonyl)-2,2-dimethyl-1,3-dioxan-5-aminium Tosylate

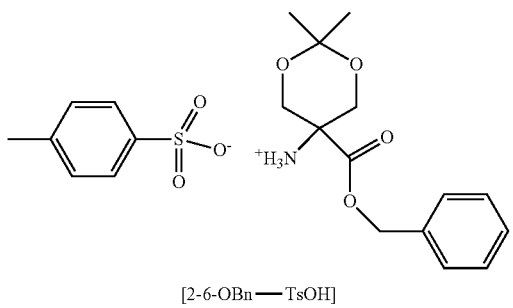

[2-6-OBn—TsOH]

This compound 2-6-OBn-TsOH is prepared following the literature procedure (*J. Pept. Sci.* 2008, 14, 1163). $^1$H NMR (400 MHz, CDCl$_3$) δ 8.76 (b, H$_3$N+), 7.72 (d, J=6.1 Hz, 2H, aromatic in TolSO$_2$OH), 7.29 (bs, 5H, Ph), 7.07 (d, J=8.0 Hz, 2H, aromatic in TolSO$_2$OH), 5.19 (s, 21H, CH$_2$Ph), 4.24 (s, 4H, 2×CH$_2$O), 2.31 (s, 3H, CH$_3$ in TolSO$_2$OH), 1.44 (s, 3H, CH$_3$), 1.40 (s, 3H, CH$_3$).

Preparation Example 4: Dipeptide Fmoc-Asp(O$^t$Bu)-D-Phe-OH Synthesis

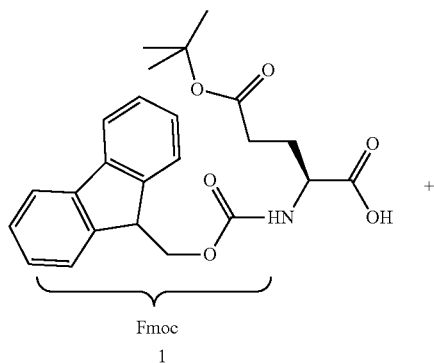

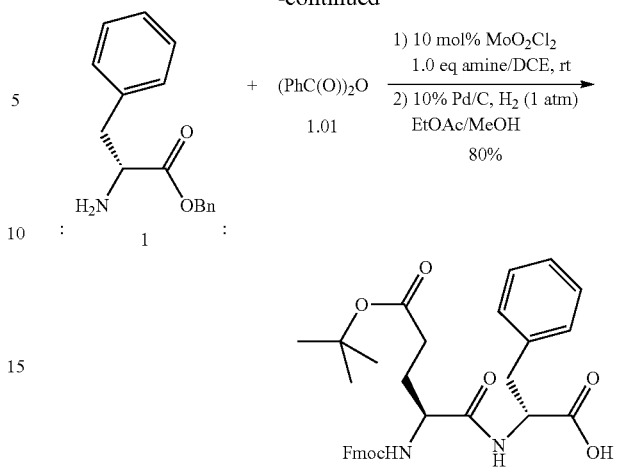

To a solution of Fmoc-Asp(O$^t$Bu)-OH (2.06 g, 5 mmol, 1.0 eq) in 1,2-dichloroethane (DCE, 10 mL) was added benzoic anhydride (1.14 g, 5.05 mmol, 1.01 eq) and MoO$_2$Cl$_2$ (100 mg, 0.5 mol, 10 mol %) at room temperature under N$_2$ atmosphere and the reaction was monitored by TLC analysis. The reaction was stirred at room temperature for 2 h till the starting amino acid was totally consumed and cooled to 0° C. A solution of D-phenylalanine benzyl ester (1.275 g, 5.0 mmol, 1.0 eq) in 5 mL of DCE was added to the above solution via syringe follow by the addition of amine base (5.0 mmol, 1.0 eq) at 0° C. The reaction mixture was allowed stir at room temperature for 30 min. Solvent was evaporated, and the remaining residue was dissolved in EtOAc (100 mL), washed with saturated aqueous NaHCO$_3$ (30 mL), H$_2$O (30 mL), brine (30 mL), and dried over Na$_2$SO$_4$. After evaporation of solvent, the remaining residue was purified by flash chromatography on silica gel to provide Fmoc-Asp(O$^t$Bu)-D-Phe-OBn (2.68 g, 81% yield) as a white solid: TLC R=0.5 (EtOAc/Hexane=1/5); $^1$H NMR (400 MHz, CDCl$_3$): δ 7.77 (d, J=7.6, 2H), 7.57 (q, J=3.6, 2H), 7.41 (t, J=7.6, 2H), 7.35-7.32 (m, 4H), 7.30-7.27 (m, 4H), 7.17 (t, J=6.0, 3H), 7.02 (t, J=6.4, 3H), 5.83 (br, 1H), 5.13 (q, J=12.0, 2H), 4.87 (q, J=7.2, 1H), 4.58-4.49 (m, 1H), 4.36 (d, J=7.2, 2H), 4.20 (t, J=7.2, 1H), 3.10 (dd, J=16.4, 5.6, 2H), 1.43 (s, 9H); $^{13}$C NMR (100 MHz, CDCl$_3$) 170.8, 170.0, 156.0, 143.8, 143.6, 141.3, 135.5, 135.0, 129.2, 128.6, 128.5, 127.7, 127.1, 125.1, 120.0, 81.9, 67.3, 67.2, 53.4, 51.1, 47.0, 37.8, 37.3, 28.0; HRMS (ESI), Calcd. for C$_{40}$H$_{42}$N$_2$NaO$_7$ ([M+Na]$^+$): 685.2889, found: 685.2887.

To a solution of Fmoc-Asp(O$^t$Bu)-D-Phe-OBn (2.0 g, 3.0 mmol, 1 equiv) in 150 mL of 1/1 (v/v) ratio of EtOAc/MeOH was added 10% Pd/C (383 mg, 10 mol %) at RT. The reaction was allowed to stir in an atmosphere of hydrogen (balloon) over 1.5 h, following which it was filtered over Celite. The Celite was washed multiple times with MeOH (30 mL), EtOAc (30 mL) and the combined filtrate was concentrated in vacuo to give 1.699 g (99%) of dipeptide Fmoc-Asp(O$^t$Bu)-D-Phe-OH as a white solid. TLC R$_f$=0.23 (EtOAc/Hex=2/1)

$^1$H NMR (300 MHz, CDCl$_3$): δ 7.75 (d, J=7.5, 2H), 7.54 (d, J=7.2, 2H), 7.39 (t, J=7.5, 2H), 7.29 (d, J=7.2, 2H), 7.23-7.16 (m, 5H), 7.06 (d, J=7.5, 1H), 6.12 (d, J=8.7, 1H), 3.21 (dd, J=9.6, 6.3, 1H), 3.06 (dd, J=9.6, 6.6, 1H), 2.72 (dd, J=16.8, 6.3, 1H), 2.57 (dd, J=16.2, 5.7, 1H), 1.43 (s, 9H); $^{13}$C NMR (100 MHz, CDCl$_3$) δ 171.4, 170.8, 170.0, 156.0, 143.7, 143.6, 141.2, 135.7, 129.2, 128.5, 127.7, 127.1, 125.1, 120.0, 81.9, 67.3, 53.4, 52.3, 51.0, 47.0, 37.9, 37.4, 29.7, 28.0; HRMS (ESI), Calcd. for C$_{33}$H$_{36}$N$_2$NaO$_7$ ([M+Na]$^+$): 595.2420, found: 595.2423.

Preparation Example 5: Dipeptide Fmoc-Arg(Mtr)-Gly-OCH$_3$ Synthesis by EDC-HOBt Coupling

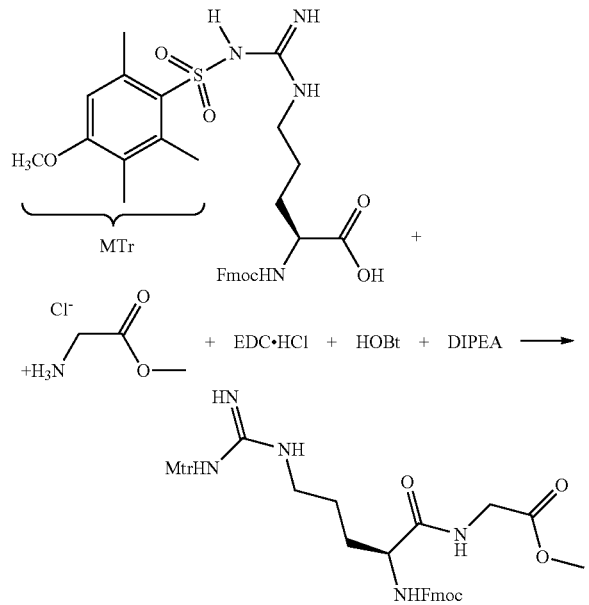

$^1$H NMR (400 MHz, CDCl$_3$): δ 7.72 (d, J=7.6, 2H), 7.63-7.54 (m, 3H), 7.25 (t, J=7.6, 2H), 7.24-7.22 (m, 1H), 6.49 (br, 1H), 6.40 (br, 1H), 6.07 (d, J=8.0 1H), 4.32 (q, J=6.8, 311), 4.14 (t, J=7.2, 1H), 4.02 (dd, J=17.6, 5.2, 1H), 3.89 (dd, J=17.6, 5.2, 1H), 3.78 (s, 3H), 3.66 (s, 3H), 3.34-3.23 (m, 2H), 2.66 (s, 3H), 2.60 (s, 3H), 2.16 (s, 3H), 2.05 (s, 3H), 1.93 (t, J=6.0, 1H), 1.72-1.60 (m, 3H), 1.27 (t, J=6.8, 1H); $^{13}$C NMR (100 MHz, CDCl$_3$) 172.8, 170.6, 158.6, 156.5, 143.8, 143.7, 141.2, 138.5, 136.6, 134.7, 134.1, 133.0, 129.1, 127.7, 125.1, 124.9, 124.3, 120.3, 120.0, 111.7, 67.1, 60.4, 55.4, 52.3, 47.0, 41.0, 40.2, 31.9, 30.0, 29.7, 25.1, 24.0, 21.0, 18.3; HRMS (ESI), Calcd. for C$_{34}$H$_{41}$N$_5$NaO$_8$S ([M+Na]$^+$): 702.2573, found: 702.2575.

Example 1

[Scheme I: Fmoc-3-6]

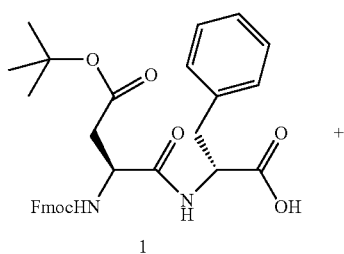

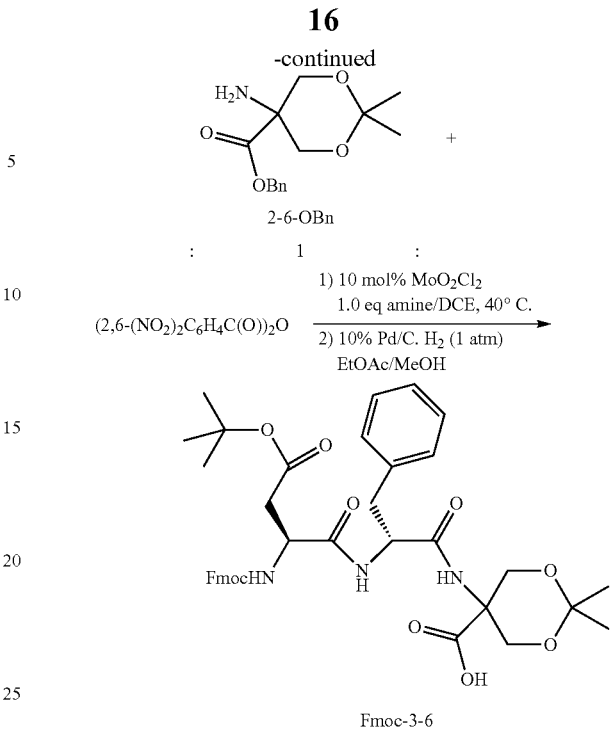

A solution of 2-6-OBn-TsOH (1.23 g, 2.8 mmol) in MeOH (5 mL) was cooled to 0° C., 1.5 eq NaHCO$_3$ was added and stirred for 1 h at rt. MeOH was evaporated and the resulting residue was re-dissolved in 10 mL ether and dried with Na$_2$SO$_4$, and filtered. The solvent was removed and dried under vacuum to obtain 2-6-OBn.

To a solution of Fmoc-Asp(O$^t$Bu)-D-Phe-OH (1.6 g, 2.8 mmol, 1.0 eq) in 1,2-dichloroethane (DCE, 5 mL) was added 2,6-dinitrobenzoic anhydride (974 mg, 2.82 mmol, 1.01 eq) and MoO$_2$Cl$_2$ (56 mg, 0.28 mmol, 10 mol %) at room temperature and gradually heated ~40° C. under N$_2$ atmosphere and the reaction was monitored by TLC analysis. The reaction was stirred at 40° C. for 2 h till the starting dipeptide was totally consumed and then cooled to 0° C. A solution of 2-6-OBn benzyl ester (743 mg, 2.8 mmol) in 4 mL DCE was added to the above solution via syringe follow by the addition of amine (2.8 mmol, 1.0 eq) at 0° C. The reaction mixture was allowed stir at room temperature for 10-12 h. Solvent was evaporated, and the remaining residue was re-dissolved in EtOAc. The organic layer was washed with saturated aqueous NaHCO$_3$ (2 mL), H$_2$O (2 mL), brine (2 mL), and dried over Na$_2$SO$_4$. After evaporation of solvent, the remaining residue was purified by silica gel flash chromatography to provide Fmoc-Asp(O$^t$Bu)-D-Phe-ADM-DOA-OBn (1.85 g, 82% yield) as a white solid. It was then re-dissolved in 80 mL of 1/1 (v/v) ratio of EtOAc/MeOH and 10% of Pd/C (242 mg, 10 mol %) was added at ambient temperature. The reaction was allowed to stir in an atmosphere of hydrogen (balloon) for 3 h, following which it was filtered thru a short plug of Celite. The Celite was washed 3 times with MeOH (15 mL), EtOAc (15 mL) and the combined filtrate was concentrated in vacuo to give 1.62 g (98%) of dipeptide Fmoc-Asp(O Bu)-D-Phe-ADMDOA-OH (Fmoc-3-6) as a white solid: $^1$H NMR (400 MHz, CDCl$_3$): δ 12.18 (b, 1H, COOH), 7.85 (d, J=7.2, 2H), 7.73-7.72 (m, 6H), 7.38-7.28 (m, 5H), 7.31-7.14 (m, 6H), 6.86 (d, J=16.0, 1H), 6.42 (d, J=5.4, 1H), 6.08 (br, 1H), 4.80 (q, J=7.4, 1H), 4.46-4.42 (m, 1H), 4.28 (d, J=12.0, 2H), 4.13 (d, J=12.0, 2H), 3.14-3.04 (m, 2H), 2.89-2.69 (m, 2H), 1.44 (s, 9H, C(CH$_3$)$_3$), 1.34 (s, 6H, CMe$_2$); TLC R$_f$=0.31 (EtOAc/Hex, 2/1); HRMS (ESI), Calcd. for C$_{39}$H$_{45}$N$_3$NaO$_{10}$ ([M+Na]$^+$): 738.3003, found: 738.3008.

[Scheme I': Fmoc-3'-6]

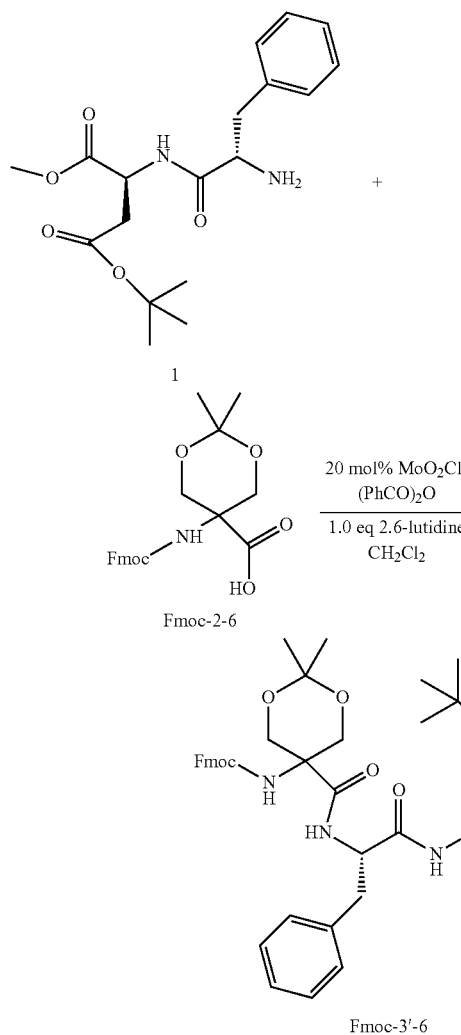

A solution of H-D-Phe-Asp(OtBu)-OMe.HCl (1-HCl) (490 mg, 1.3 mmol, 1.01 eq) in MeOH (8 mL) was cooled to 0° C., 1.5 eq NaHCO$_3$ was added and stirred for 1 h at rt. MeOH was evaporated and the resulting residue was re-dissolved in 15 mL THF and dried with Na$_2$SO$_4$, and filtered. The solvent was removed and dried under vacuum to obtain D-Phe-Asp(OtBu)-OMe (1).

In a dry 50-mL, two-necked, round-bottomed flask was charged with MoO$_2$Cl$_2$ (50 mg, 0.25 mmol, 20 mol %) in anhydrous CH$_2$Cl$_2$ (12 mL). To the above solution, Fmoc-2-6 (497.1 mg, 1.25 mmol) was added at ambient temperature followed by addition of benzoic anhydride (342 mg, 1.28 mmol), and heated at 40° C. for 6 h then cooled to 0° C.

A solution of D-Phe-Asp(OtBu)-OMe (441.8 mg, 1.26 mmol) in DCM (5 mL) was added to above solution at 0° C. and the reaction mixture was gradually warmed to ambient temperature and stirred for 2.5 h. Afterward, 145 µL of 2,6-lutidine was added and the mixture continued to stir for an additional 4.5 h. The reaction was then quenched with water (16 mL). The organic phase was separated and the aqueous phase was extracted with CH$_2$Cl$_2$ (50 mL×2). The combined organic layers were dried over anhydrous Na$_2$SO$_4$, filtered, and concentrated. The crude residue was purified by column chromatography on silica gel (EtOAc/hexanes, 2/3) to give Fmoc-protected tripeptide (Fmoc-3'-6) (695 mg, 76%): TLC R$_f$ 0.2 (EtOAc/hexanes, 3:7); $^1$H NMR (400 MHz, CDCl$_3$) δ 8.15 (bs, NH, 1H), 7.88 (d, J=7.2 Hz, 2H), 7.57 (d, J=7.2 Hz, 2H), 7.41-7.28 (m, 4H), 7.16-7.13 (m, 5H), 7.10 (bs, NH, 1H), 4.82 (d, J=6.6 Hz, 1H), 4.76 (d, J=5.8 Hz, 1H), 4.61-4.57 (m, 2H), 4.30 (d, J=11.8 Hz, 2H, CH$_2$O), 4.17 (t, J=6.4 Hz, 1H), 3.57 (s, 3H), 4.05 (d, J=12.0 Hz, 2H, CH$_2$O), 3.33 (dd, J=14.0, 6.8 Hz, 1H), 3.09 (dd, J=14.0, 8.0 Hz, 1H), 2.88-2.62 (m, 2H), 1.38 (s, 9H), 1.35 (s, 3H, CH$_3$), 1.31 (s, 3H, CH$_3$); HRMS (ESI) calcd for C$_{40}$H$_{47}$N$_3$NaO$_{10}$ (M+Na$^+$): 752.3159; found: 752.3166.

[Scheme I': Fmoc-3'-6]

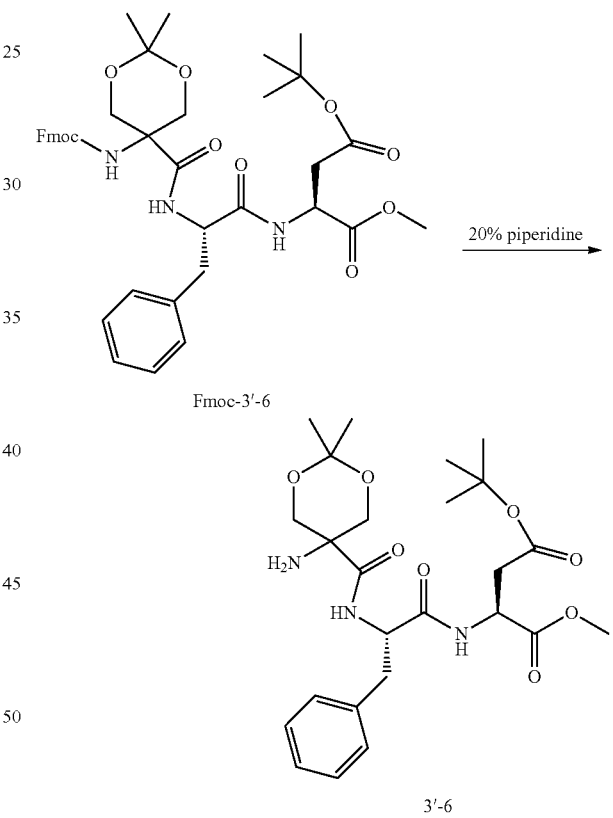

A solution of 910 mg (1.25 mmol) of the Fmoc-protected tripeptide (Fmoc-3'-6) was treated with 20% piperidine in DCM (5 mL) for 1 hour at ambient temperature. After removal of piperidine by co-evaporation with methanol (5 mL), the crude product was dried in vacuo and then purified by column chromatography on silica gel to obtain 534.2 mg (84%) of the tripeptide (3'-6): TLC R$_f$ 0.31 (EtOAc/hexanes, 9:1); $^1$H NMR (400 MHz, CDCl$_3$) δ 8.26 (d, J=8.0 Hz, 1H, NH), 7.20-7.14 (m, 5H), 7.00 (d, J=8.2 Hz, 1H, NH), 4.77-4.74 (m, 1H), 4.60-4.56 (m, 1H), 4.10 (d, J=12.0 Hz, 2H, CH$_2$O), 3.90 (d, J=12.0 Hz, 2, 2H, CH$_2$O), 3.64 (s, 3H, OCH$_3$), 3.12 (dd, J=14.0, 6.4 Hz, 1H), 2.96 (dd, J=14.0, 8.2

Hz, 1H), 2.80 (dd, J=16.0, 4.0 Hz, 1H), 2.46 (dd, J=16.0, 4.6 Hz, 1H), 1.35 (s, 9H, C(CH$_3$)$_3$), 1.37 (s, 3H, CH$_3$), 1.35 (s, 3H, CH$_3$); HRMS (ESI) calcd for C$_{25}$H$_{37}$N$_3$O$_8$(M+H$^+$): 508.2659; found: 508.2654.

Example 2

[Scheme II: Fmoc-5-6]

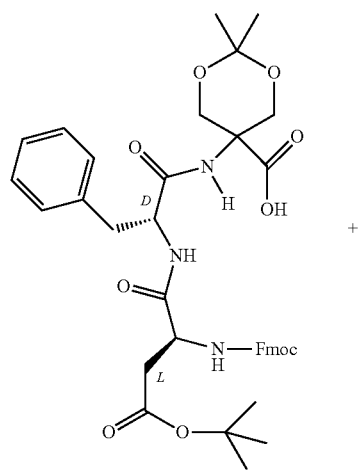

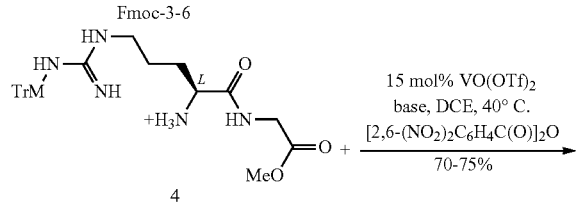

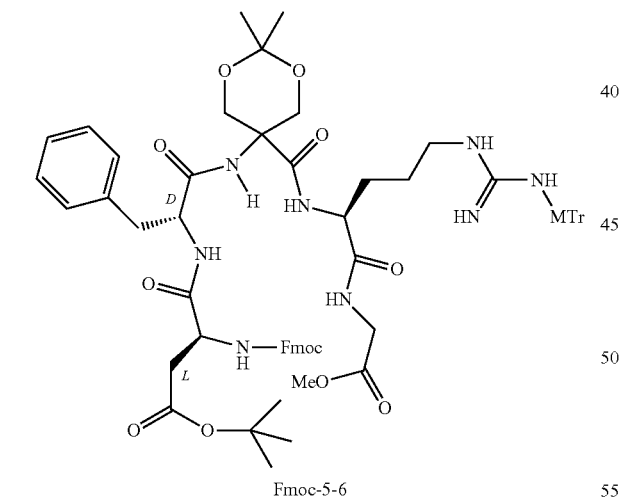

To a solution of Fmoc-Asp(O$^t$Bu)-D-Phe-ADMDOA-OH, Fmoc-3-6, (715.0 mg, 1 mmol, 1.0 equiv) in 1,2-dichloroethane (DCE, 7 mL) was added 2,6-dinitrobenzoic anhydride (414.3 mg, 1.01 mmol, 1.01 equiv) and VO(OTf)$_2$ (55 mg, 0.15 mmol, 15 mol %) at ambient temperature. The reaction mixture was then heated to 40° C. under N$_2$ atmosphere and the reaction was monitored by TLC analysis. The reaction was stirred at 40° C. for 4 h till the starting Fmoc-3-6 was totally consumed and and then cooled to 0°

C. A solution of NH$_2$-Arg(Mtr)-Gly-OCH$_3$ (457.8 mg, 1.0 mmol) in 3 mL DCE was added to the above solution via a syringe followed by the addition of an amine base (1.0 mmol, 1.0 equiv) at 0° C. The reaction mixture was allowed to stir at ambient temperature for 10-12 h. The reaction solvent was evaporated, and the remaining residue was re-dissolved in EtOAc (85 mL). The organic layer was washed with saturated, aqueous NaHCO$_3$ (16 mL), H$_2$O (16 mL), brine (10 mL), and the dried over Na$_2$SO$_4$. After evaporation of solvent, the remaining residue was purified by flash column chromatography on silica gel to provide Fmoc-Asp(O$^t$Bu)-D-Phe-ADMDOA-Arg(Mtr)-Gly-OCH$_3$, Fmoc-5-6, (866.0 mg, 75% yield): TLC R$_f$ 0.42 (EtOAc); δ 7.77 (d, 2H, J=7.4 Hz), 7.55 (m, 2H), 7.36 (t, 2H, J=7.6 Hz), 7.30-7.18 (m, 8H), 6.65 (br, 1H), 6.59 (br, 1H), 4.77 (br, 1H), 4.64-4.56 (m, 1H), 4.39 (t, 1H, J=6.8 Hz), 4.35-4.23 (m, 1H), 4.19 (d, J=12.0 Hz, 2H, CH$_2$O), 4.15 (t, 1H, J=7.2 Hz), 4.18-4.07 (m, 3H), 3.78 (s, 3H, OCH$_3$), 3.66-3.56 (m, 1H), 3.53 (s, 3H, CO$_2$CH$_3$), 3.43-3.39 (m, 1H), 3.19-3.10 (m, 2H), 3.06-2.94 (m, 1H), 2.64 (s, 3H), 2.50 (s, 3H), 2.26-2.08 (m, 2H), 2.07 (s, 3H), 1.41 (s, 9H, C(CH$_3$)$_3$), 1.38 (s, 3H, CH$_3$), 1.36 (s, 3H, CH$_3$); HRMS (ESI), calculated for C$_{58}$H$_{74}$N$_8$NaO$_{15}$S ([M+Na]$^+$): 1177.4892, found: 1177.4890.

[Scheme II'-Fmoc-5'-6]

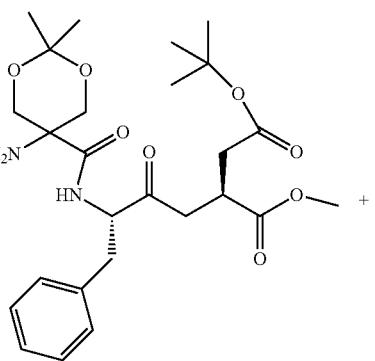

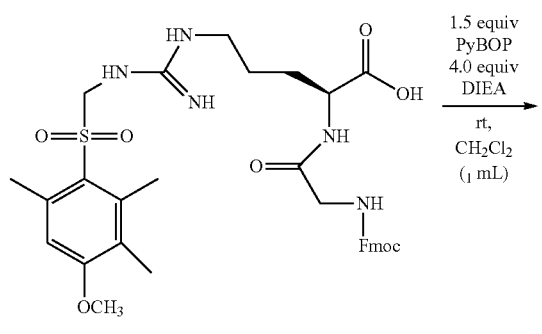

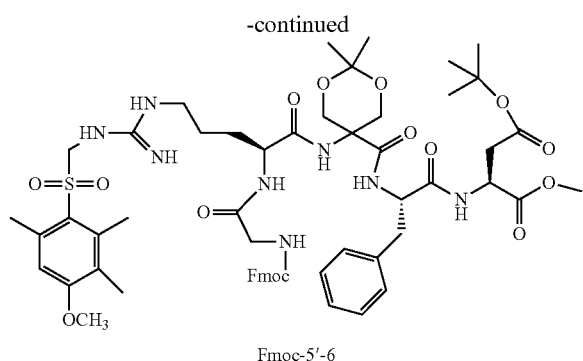

Fmoc-5'-6

In a dry 25-mL, two-necked, round-bottomed flask was charged with catalyst (10-15 mol %) and a coupling reagent (1.5 equiv) in DCM (5 mL/mmol) and treated under stirring with DIEA (4.0 equiv) at 0° C. for 5 min. Fmoc-Gly-Arg (Mtr)-OH (4) (748.2 mg, 1.1 mmol) was added at 0° C. for 20 min, followed by addition of tripeptide (3'-6) (558.0 mg, 1.1 mmol). The ice bath was then removed after 20 min and the stirring was continued at ambient temperature for 6 days. The crude product was dried in vacuo and purified by column chromatography on silica gel to obtain 890.2 mg (70%; by $MoO_2Cl_2$/4-nitrobenzoic anhydride) of Fmoc-protected pentapeptide, Fmoc-5'-6: TLC $R_f$ 0.66 (EtOAc/MeOH, 9.5:0.5); $^1$H NMR (400 MHz, $CDCl_3$) δ 7.73 (d, J=8.0, 1H, NH), 7.73 (d, J=8.2, 2H), 7.51 (d, J=6.4, 1H, NH), 7.55 (d, J=7.2, 2H), 7.40 (bd, 1H, NH), 7.33 (d, J=8.0, 2H), 7.34-7.12 (m, 2H), 7.13-7.04 (m, 6H), 6.82 (d, J=7.6 Hz, 1H, NH), 6.55 (s, 1H), 6.40 (bs, 2H), 4.85 (dd, J=14.2, 6.4 Hz, 1H), 4.69 (dd, J=14.0, 8.4 Hz, 1H), 4.43-4.22 (m, 3H), 4.12 (d, J=12.0 Hz, 2H, $CH_2O$), 4.17-4.13 (m, 1H), 3.87-3.86 (m, 1H), 3.76 (s, 31H, $OCH_3$), 3.73-3.71 (m, 1H), 3.63 (s, 3H, $CO_2CH_3$), 3.54-3.46 (m, 1H), 3.43-3.36 (m, 2H), 3.20-3.16 (m, 1H), 3.08 (dd, J=14.0, 9.3 Hz, 1H), 2.71 (m, 1H), 2.66 (t, J=8.0 Hz, 1H, NH), 2.64 (s, 3H, $CH_3$), 2.61 (s, 3H, $CH_3$), 2.12 (bs, 1H, NH), 2.08 (s, 3H, $CH_3$), 1.74-1.66 (m, 2H), 1.47-1.45 (m, 2H), 1.38 (s, 9H, C$(CH_3)_3$), 1.41 (s, 3H, $CH_3$), 1.39 (s, 3H, $CH_3$); HRMS (ESI) calcd for $C_{58}H_{75}N_8O_{15}S$ (M+H$^+$): 1155.5073; found: 1155.5079.

Example 3

[Scheme III: 6-6]

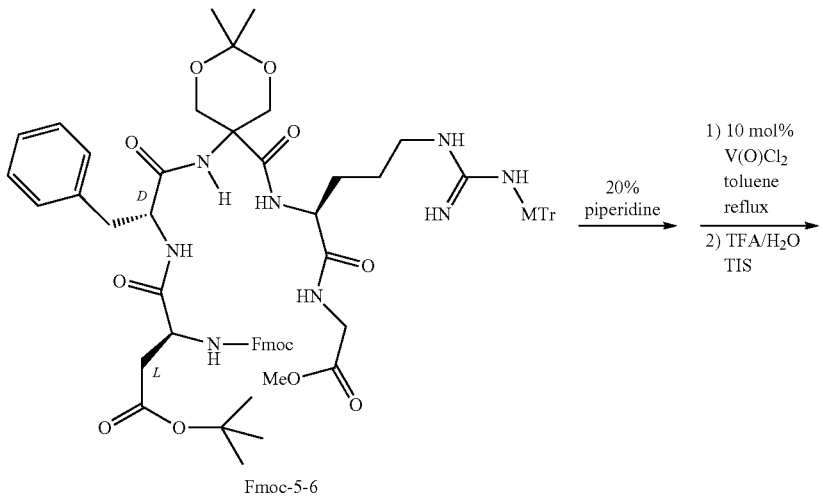

Fmoc-5-6

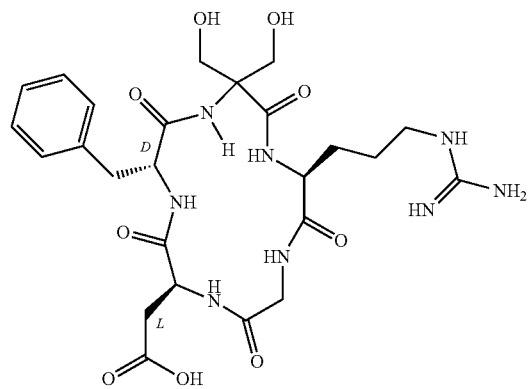

6-6

After Fmoc deprotection and cyclization of Fmoc-5-6, the following compound t-Boc-6-6-MTr was obtained.

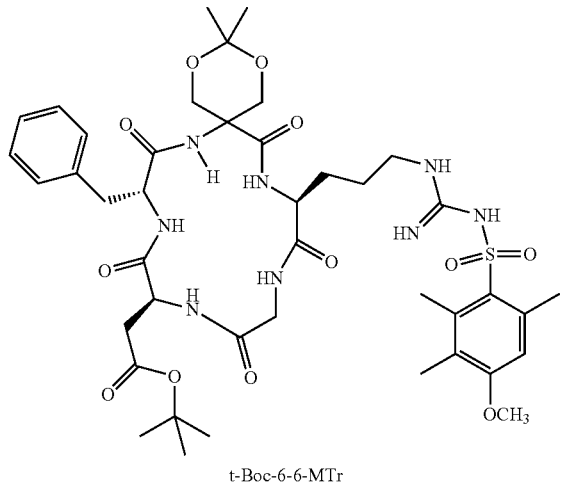 [SMILES: COc1cc(C)c(S(=O)(=O)NC(=N)NCCC[C@@H]2NC(=O)C3(COC(C)(C)OC3)NC(=O)[C@@H](Cc3ccccc3)NC(=O)[C@H](CC(=O)OC(C)(C)C)NC(=O)CNC2=O)c(C)c1C]

t-Boc-6-6-MTr

A solution of 57.8 mg (0.05 mmol) of the Fmoc-protected pentapeptide (Fmoc-5-6) was treated with 20% piperidine in DCM (3 mL) for 1 hour at ambient temperature. After removal of piperidine by co-evaporation with methanol (3 mL), the crude product was dried in vacuo. The resulting crude product was subjected to an intramolecular amide bond formation by treatment with 10 mol % V(O)Cl$_2$, Zr(O)Cl$_2$, V(O)(acac)$_2$, or Ti(O)(acac)$_2$ in refluxed toluene for 10 h. The resulting crude mixture was cooled to ambient temperature and concentrated. The crude residue (t-Boc-6-6-MTr) was re-dissolved in trifluoroacetic acid (7 mL) and H$_2$O (1.5 mL) and then treated with thioanisole (1.5 mL). The mixture was induced precipitation with di-isopropyl ether (7 mL) and the resulting solid was washed with di-isopropyl ether and dried in vacuo to obtain the cyclopeptide (6-6). The cyclic pentapeptide can be further purified by HPLC on a reverse phase C-18 column (gradient: 95/5 to 80/20, H$_2$O/CH$_3$CN) to give 22.3 mg (75% yield) of pure 6-6.

Data for t-Boc-6-6-MTr: TLC: R$_f$ 0.39 (EtOAc/MeOH, 3/1); $^1$H NMR (400 MHz, CDCl$_3$): δ 8.02 (s, 1H, C═NH), 7.84 (bs, 1H, NH), 7.59 (bs, 1H, NH), 7.39-7.19 (m, 6H), 6.99 (br, 1H), 6.62 (br, 1H, NH), 6.30 (br, 1H, NH), 4.80-4.72 (m, 1H), 4.72-4.63 (m, 1H), 4.30-4.25 (m, 1H), 4.24 (d, J=11.8, 2H, CH$_2$O), 4.16 (d, J=11.8, 2H, CH$_2$O), 4.10-4.07 (m, 2H), 3.61-3.56 (m, 2H), 3.54-3.25 3.34 (m, 2H, CH$_2$-quanidine), 3.45 (s, 3H, OCH$_3$), 3.19-3.06 (m, 1H), 3.01-2.82 (m, 2H), 2.70 (s, 3H, CH$_3$), 2.61 (s, 3H, CH$_3$), 2.14 (s, 3H, CH$_3$), 1.78-1.63 (m, 2H), 1.48-1.33 (m, 2H), 1.50 (s, 9H, C(CH$_3$)$_3$), 1.37 (s, 3H, CH$_3$), 1.34 (s, 3H, CH$_3$); HRMS (ESI), calculated for C$_{42}$H$_{61}$N$_8$O$_{12}$S ([M+H]$^+$): 901.4130, found: 901.4133.

After simultaneous MTR, tert-Boc and acetonide deprotection of t-Boc-6-6-MTr, Compound 6-6 was obtained.

Data for Compound 6-6: $^1$H NMR (400 MHz, CDCl$_3$) δ 9.66 (bs, 2H, G-NH$_2$$^+$), 8.30 (bs, 1H, G-NH), 7.81 (bd, J=8.0, 1H, amide NH), 7.70 (d, J=8.2, 1H, amide NH), 7.68 (d, J=8.2, 1H, amide NH), 7.58 (t, J=8.0, 1H, amide NH), 7.36 (d, J=8.2, 1H, amide NH), 7.19-7.14 (m, 5H, Ph), 6.90 (bs, 2H, G-NH$_2$), 4.69 (dd, J=16.0, 7.6, 1H), 4.57 (bt, 1H), 4.32 (bs, 2H), 4.20 (s, 2H, CH$_2$O), 4.19 (dd, J=16.0, 7.4, 1H), 4.03 (s, 2H, CH$_2$O), 3.39 (t, J=14.8 Hz, 2H), 3.19-3.11 (m, 4H), 2.70 (dd, J=16.2, 7.4, 1H), 2.60 (dd, J=16.2, 10.2, 1H), 1.82-1.77 (m, 2H), 1.53-1.51 (m, 2H); HRMS (ESI) calcd for C$_{25}$H$_{37}$N$_8$O$_9$ (M$^+$+H): 593.2678; found: 593.2680; HPLC analysis: (C18, 250×4.6 mm, 0.5 (mL/min), λ=254 nm). a. 1% TFA in H$_2$O/ACN (95:5) 30 min; b. 1% TFA in H$_2$O/ACN (5:95) 31-60 min; t$_R$ 31.5, 39.6 min.

[Scheme III′: 6′-6]

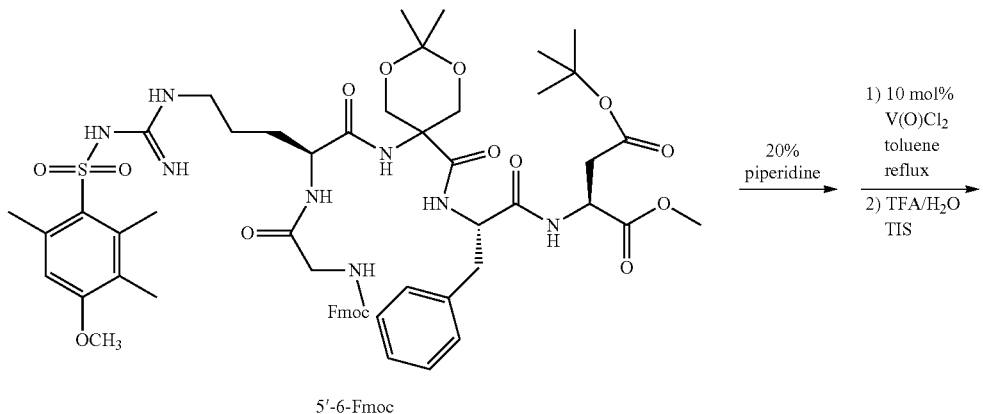

5′-6-Fmoc

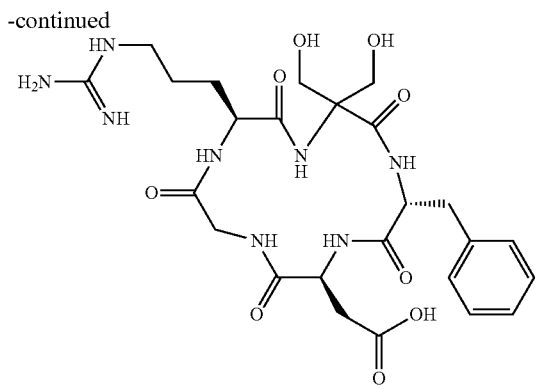

6'-6

A solution of 58.0 mg (0.05 mmol) of the Fmoc-protected pentapeptide (Fmoc-5'-6) was treated with 20% piperidine in DCM (3 mL) for 1 hour at ambient temperature. After removal of piperidine by co-evaporation with methanol (3 mL), the crude product was dried in vacuo. The resulting crude product was subjected to an intramolecular amide bond formation by treatment with 10 mol % V(O)Cl$_2$, Zr(O)Cl$_2$, V(O)(acac)$_2$, or Ti(O)(acac)$_2$ in refluxed toluene for 10 h. The resulting crude mixture was cooled to ambient temperature and concentrated. The crude residue (MTr-6'-6-t-Boc) was re-dissolved in trifluoroacetic acid (7 mL) and H$_2$O (1.5 mL) and then treated with thioanisole (1.5 mL). The mixture was induced precipitation with di-isopropyl ether (7 mL) and the resulting solid was washed with di-isopropyl ether and dried in vacuo to obtain the cyclopeptide (6'-6). The cyclic pentapeptide can be further purified by HPLC on a reverse phase C-18 column (gradient: 95/5 to 80/20, H$_2$O/CH$_3$CN) to give 25.2 mg (86% yield) of pure 6'-6.

After Fmoc deprotection and cyclization of 5'-6-Fmoc, the following compound MTr-6'-6-t-Boc was obtained.

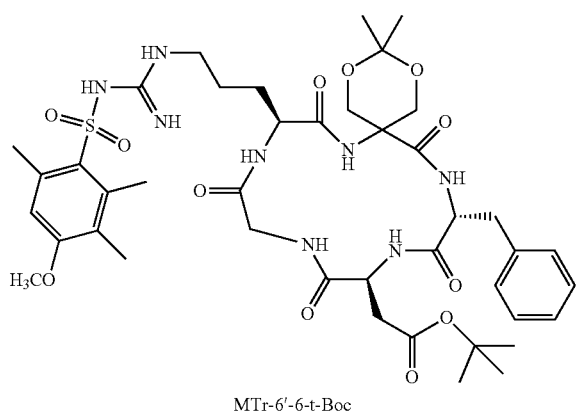 [SMILES: COc1cc(C)c(S(=O)(=O)NC(=N)NCCC[C@@H]2NC(=O)CNC(=O)[C@H](CC(=O)OC(C)(C)C)NC(=O)[C@@H](Cc3ccccc3)NC(=O)C3(COC(C)(C)OC3)NC2=O)c(C)c1C]

MTr-6'-6-t-Boc

Data for Mtr-6'-6-t-Boc: $^1$H NMR (400 MHz, CDCl$_3$) δ 7.66 and 7.31 (m, 2H, imine and amide), 7.21-7.15 (m, 5H, Ph group), 6.46 (s, 1H, amide), 6.30 (br, 2H, amide), 4.82 (dd, J=6.0, 6.9 Hz, 1H), 4.56-4.52 (m, 1H), 4.42-4.31 (m, 1H), 4.16 (d, J=11.8 Hz, 2H, CH$_2$O), 3.96 (d, J=12.0 Hz, 2H, CH$_2$O), 3.82-3.79 (m, 1H), 3.78 (s, 3H, OCH$_3$-Ph), 3.35-3.18 (m, 3H), 2.78-2.69 (m, 1H), 2.73 (t, J=8.4 Hz, 2H, CH$_2$-guanidine), 2.64 (s, 3H, CH$_3$-Ph), 2.62 (s, 3H, CH$_3$-Ph), 2.38 (t, J=10.4 Hz, 1H), 2.05 (s, 3H, CH$_3$-Ph), 1.62-1.54 (m, 2H), 1.40 (m, 2H), 1.39 (s, 3H, CH$_3$), 1.37 (s, 9H, t-Bu), 1.33 (s, 3H, CH$_3$); R$_f$ 0.45 (EtOAc/MeOH, 9/1); HRMS (ESI) calcd for C$_{42}$H$_{61}$N$_8$O$_{12}$S (M+H): 901.4130; found: 901.4132.

After MTR, tert-Boc and acetonide deprotection of MTr-6'-6-t-Boc, Compound 6'-6 was obtained.

Data for Compound 6'-6: $^1$H NMR (400 MHz, CDCl$_3$) δ 10.07 (bs, 2H, G-NH$_2$$^+$), 8.24 (bs, 1H, G-NH), 7.79 7.50 (bd, J=8.4, 1H, amide NH), 7.70 (d, J=8.2, 1H, amide NH), 7.65 (d, J=8.2, 1H, amide NH), 7.56 (t, J=8.0, 1H, amide NH), 7.49 (d, J=8.2, 1H, amide NH), 7.24-7.15 (m, 5H, Ph), 4.71 (dd, J=13.2, 6.8, 1H), 4.51 (bt, 1H), 4.28 (bs, 2H), 4.24 (dd, J=15.8, 7.0, 1H), 3.88 (s, 2H), 3.80 (s, 2H), 3.28 (t, J=13.8 Hz, 1H), 3.20-3.05 (m, 3H), 2.72 (dd, J=16.0, 7.6 Hz, 1H), 2.63 (dd, J=16.0, 10.4, 1H), 1.74 (nm, 2H), 1.41 (m, 2H); HRMS (ESI) calcd for C$_{25}$H$_{37}$N$_8$O$_9$ (M$^+$+H): 593.2678; found: 593.2681; HPLC analysis: (C18, 250×4.6 mm, 0.5 mL/min, λ=254 nm). a. 1% TFA in H$_2$O/ACN (90:10) 30 min; b. 1% TFA in H$_2$O/ACN (10:90) 31-60 min; t$_R$ 32.1, 40.0 min.

The cyclo-pentapeptide prepared in the aforesaid examples can be used with an excipient or a metal (II) sulfate to form a pharmaceutical or cosmetic composition, wherein the metal (II) sulfate can be Cu$^{2+}$ sulfate or V(O)$^{2+}$ sulfate.

Although the present invention has been explained in relation to its preferred embodiment, it is to be understood that many other possible modifications and variations can be made without departing from the spirit and scope of the invention as hereinafter claimed.

What is claimed is:

1. A cyclopeptide represented by the following formula (I) or (I'):

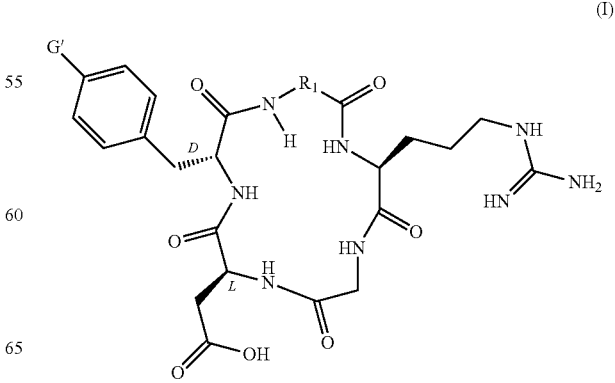

(I)

(I')

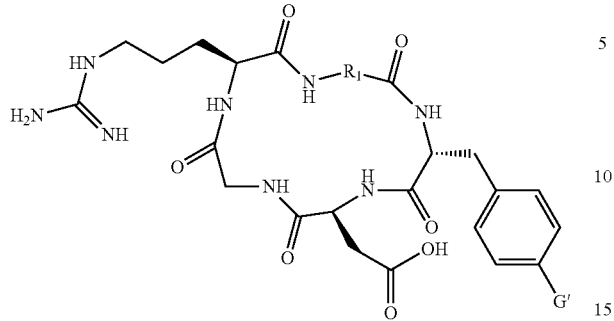

wherein,

R$_1$ is

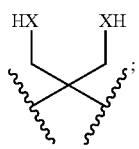

X is O, S, or N—R$_2$, in which R$_2$ is H, C$_{1-6}$ alkyl, (CH$_2$CH$_2$O)$_n$H, —C(=O)—C$_{1-10}$ alkyl, or C(=O)(C$_2$H$_4$)$_2$C(=O)O(C$_2$H$_4$O)$_n$H, in which n=1-3; and G' is H or OH.

2. The cyclopeptide of claim 1, wherein X is O, S, or N—R$_2$, in which R$_2$ is H, C$_{1-6}$ alkyl, —C(=O)—C$_{4-10}$ alkyl, (CH$_2$CH$_2$O)$_n$H or C(=O)(C$_2$H$_4$)$_2$C(=O)O(C$_2$H$_4$O)$_n$H, in which n=1-3.

3. The cyclopeptide of claim 1, wherein X is O.

4. The cyclopeptide of claim 1, which is represented by the following formula (I-1) or (I'-1):

(I-1)

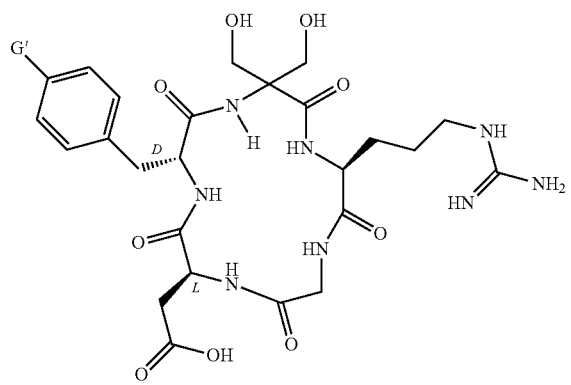

(I'-1)

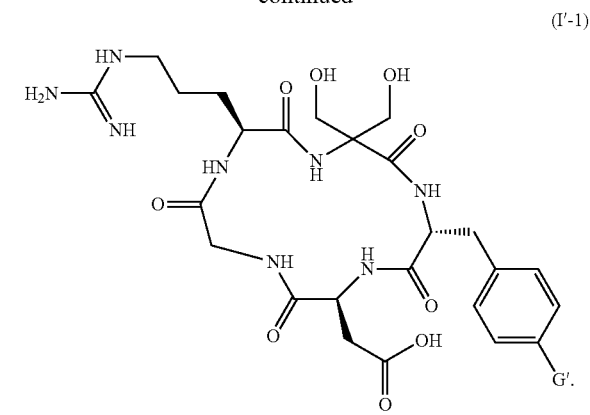

5. A pharmaceutical or cosmetic composition, comprising:
an excipient or a metal (II) sulfate; and
a cyclopeptide represented by the following formula (I) or (I'):

(I)

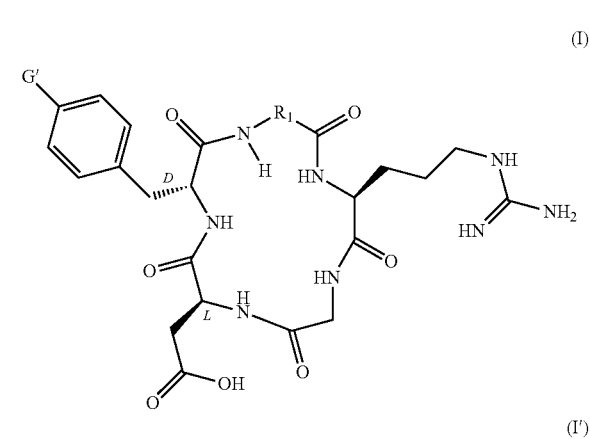

(I')

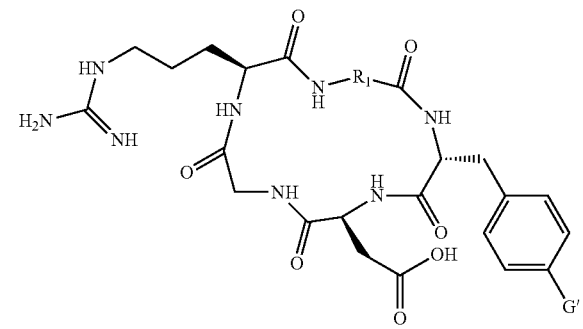

wherein,

R$_1$ is

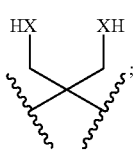

X is O, S, or N—R$_2$, in which R$_2$ is H, C$_{1-6}$ alkyl, (CH$_2$CH$_2$O)$_n$H, —C(=O)—C$_{1-10}$ alkyl, or C(=O)(C$_2$H$_4$)$_2$C(=O)O(C$_2$H$_4$O)$_n$H, in which n=1-3; and G' is H or OH.

6. The pharmaceutical or cosmetic composition of claim 5, wherein the metal (II) sulfate is Cu$^{2+}$ sulfate or V(O)$^{2+}$ sulfat.

7. The pharmaceutical or cosmetic composition of claim 5, wherein the compound of formula (I) or (I') is represented by the following formula (I-1) or (I'-1):

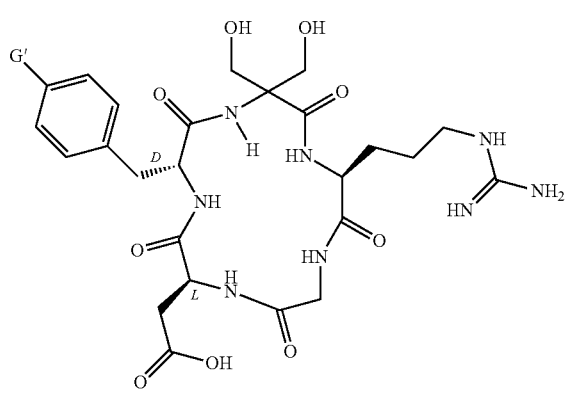
(I-1)

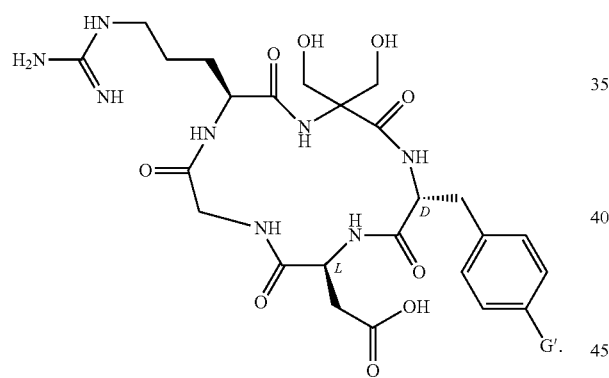
(I'-1)

8. A method for preparing a cyclopeptide, comprising the following steps:

(A) providing compounds represented Icy the following formulas (II-1) or (II'-1) and (II-2),

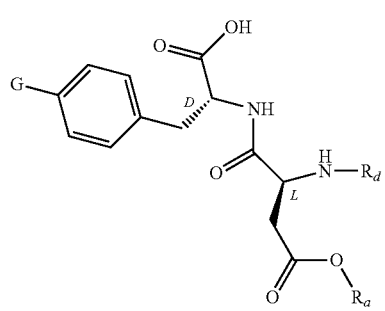
(II-1)

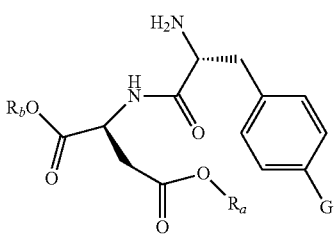
(II'-1)

R$_c$—NH—R$_1$—COOH   (II-2)

wherein, each of R$_a$ and R$_b$ independently is alkyl, cycloalkyl, aryl or heteroaryl;
each of R$_c$ and R$_d$ is a protection group;
R$_1$ is

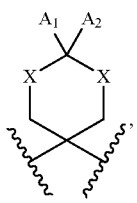

in which each of A$_1$ and A$_2$ independently is H, C$_{1-6}$ alkyl or esters, or A$_1$, A$_2$ and carbon attached to A$_1$ and A$_2$ together form C$_{5-8}$ cycloalkyl; X is O, S, or —N—R$_2$, in which R$_2$ is H, C$_{1-6}$ alkyl, (CH$_2$CH$_2$O)$_n$H, —C(=O)—C$_{1-10}$ alkyl, or C(=O)(C$_2$H$_4$)$_2$C(=O)O(C$_2$H$_4$O)$_n$H, in which n=1-3; and
G is H or Ot-Bu;

(B) performing a reaction between the compounds of formulas (II-1) or (II'-1) and (II-2), to obtain a compound represented by the following formula (II-3) or (II'-3), respectively,

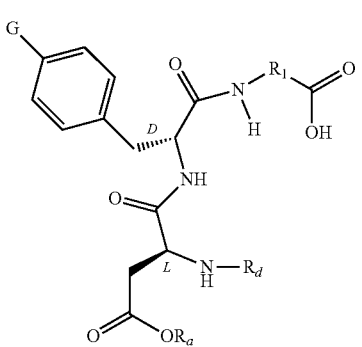
(II-3)

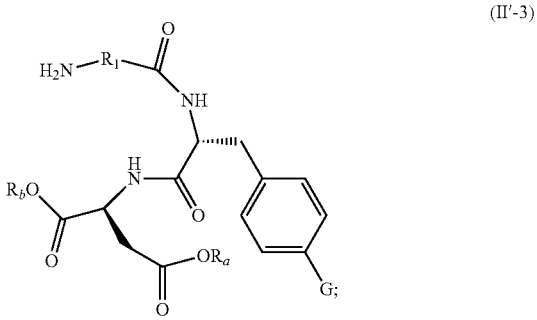
(II'-3)

(C) performing a reaction between the compound of formula (II-3) or (II'-3) and a compound represented by the following formula (II-4) or (II'-4), respectively, to obtain a compound represented by the following formula (II-5), and (II'-5), respectively,

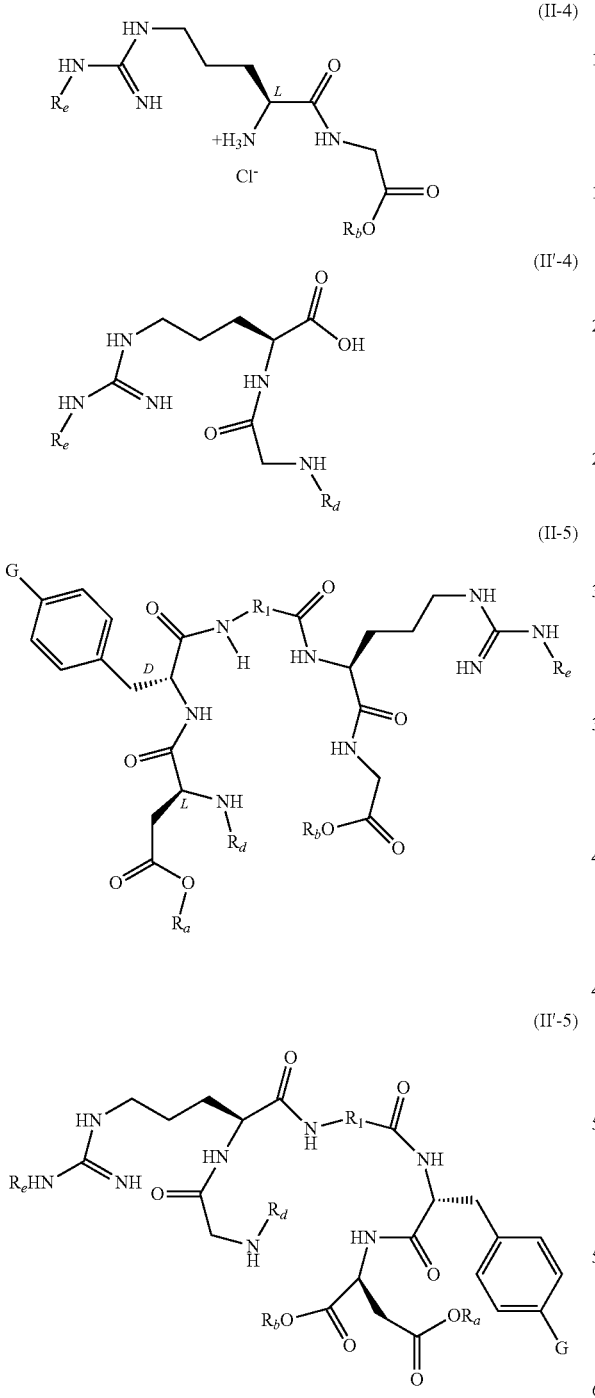

each of $R_d$ and $R_e$ independently is a protection group; and (D) performing a cyclization reaction of the compound of formula (II-5) or (II'-5) with a catalyst of formula (III), to obtain a compound represented by the following formula (I) or (I'), respectively,

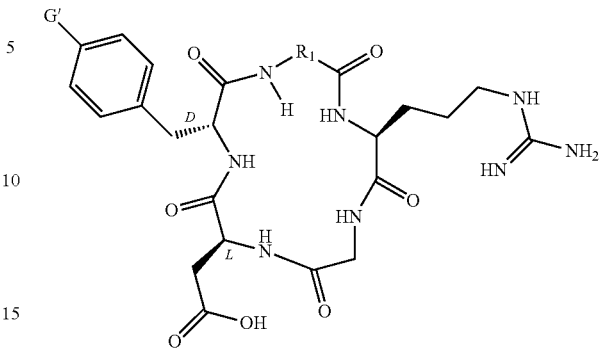

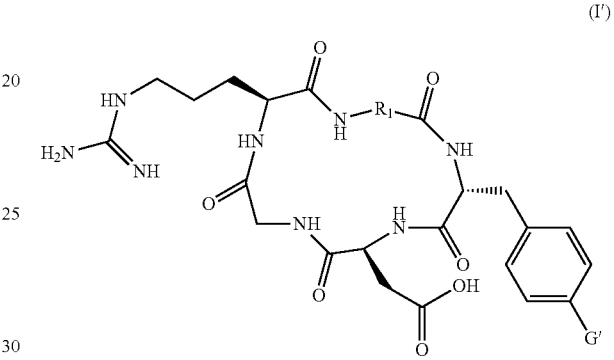

$$M(O)_m L^1_y L^2_z \quad (III)$$

wherein M is a metal selected from the group consisting of IVB, VB, VIB and actinide groups;

$L^1$ and $L^2$ respectively is a ligand;

m and y respectively are integers of greater than or equal to 1;

z is an integer of greater than or equal to 0; and

G' is H or OH.

9. The method of claim 8, wherein $L^1$ is selected from the group consisting of Cl, OTf, OTs, $NTf_2$, halogen, RC(O) CHC(O)R, OAc, $OC(O)CF_3$, OEt, O-iPr, and butyl, in which R is alkyl.

10. The method of claim 8, wherein $L^2$ is selected from the group consisting of Cl, $H_2O$, $CH_3OH$, EtOH, THF, $CH_3CN$ and

.

11. The method of claim 8, wherein $R_c$ and $R_d$ are Fmoc; and $R_e$ is MTr.

12. The method of claim 8, wherein the reaction between the compounds of formulas (II-1) or (II'-1) and (II-2) or the reaction between the compound of formula (II-3) and (II-4) or (II'-3) and (II'-4) is performed with the catalyst of formula (III).

13. The method of claim 8, wherein M is a group IVB transition element, m is 1 and y is 2.

14. The method of claim 8, wherein M is a group VB transition element, m is 1 and y is 2 or 3.

15. The method of claim 8, wherein M is a group VIB transition element, m is 1 and y is 4.

16. The method of claim 8, wherein M is a group VIB transition element, m is 2 and y is 2.

17. The method of claim 8, wherein M is selected from the actinide group, in is 2 and y is 2.

18. The method of claim 8, wherein the catalyst of formula (III) is $MoO_2Cl_2$, $V(O)OCl_2$, $V(O)(OAc)_2$, $V(O)(O_2CCF_5)_2$, $Ti(O)(acac)_2$, $Zr(O)Cl_2$, $Hf(O)Cl_2$, $Nb(O)Cl_2$, $MoO_2(acac)_2$, $V(O)(OTs)_2$, $VO(OTf)_2$ or $V(O)(NTf_2)_2$.

19. The method of claim 8, wherein z is 0.

20. The method of claim 8, wherein the compound of formula (I) or (I') is represented by the following formula (I-1) or (I'-1):

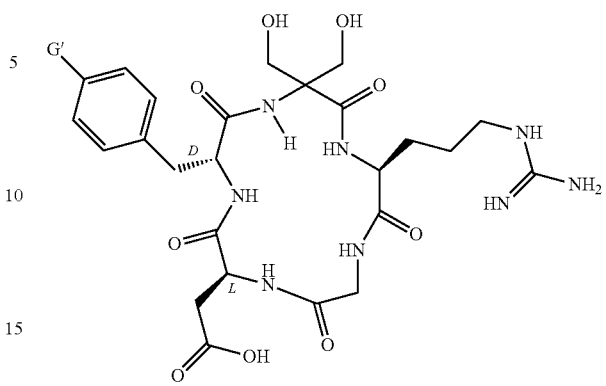

(I-1)

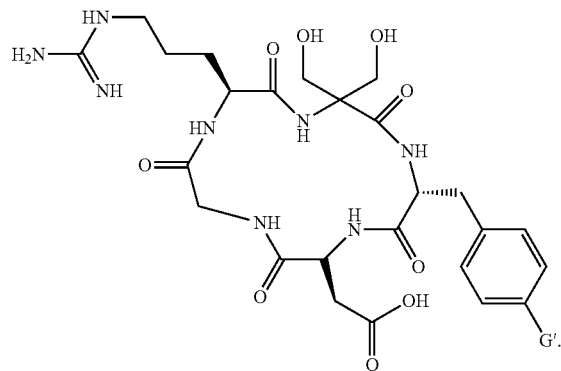

(I'-1)

* * * * *